United States Patent [19]
Makino et al.

[11] Patent Number: 5,651,997
[45] Date of Patent: Jul. 29, 1997

[54] ANTACID COMPOSITIONS

[75] Inventors: Tadashi Makino, Ibaraki; Shigeyuki Marunaka; Soichiro Imoto, both of Osaka, all of Japan

[73] Assignee: Takeda Chemical Industries, Ltd., Osaka, Japan

[21] Appl. No.: 712,798

[22] Filed: Sep. 12, 1996

Related U.S. Application Data

[63] Continuation of Ser. No. 288,608, Aug. 10, 1994, abandoned.

[30] Foreign Application Priority Data

Aug. 11, 1993 [JP] Japan .................... 5-220711

[51] Int. Cl.$^6$ ............... A61K 33/06; A61K 33/10; A61K 33/08; A61K 33/00; A61K 31/13
[52] U.S. Cl. ............... 424/682; 424/686; 424/692; 424/715; 514/666
[58] Field of Search ................ 424/682, 686, 424/692, 715; 514/666

[56] References Cited

U.S. PATENT DOCUMENTS 4,786,505  11/1988  Lovgren et al. ............ 424/468

FOREIGN PATENT DOCUMENTS 50-101520  8/1975  Japan .
59-210012  11/1984  Japan .

OTHER PUBLICATIONS

CA102: 172558, Parab et al, 1985.

CA120: 330963, Kim et al., 1993.

"Arzneimittel gegen Hyperazität (Antazida)", Helwig Arzneimittel, 6th edition, vol. 11, 1988, pp. 38–6 through 38–17, chapter 38.3.

"Organic Chemical Drugs and their Synonyms", M. Negwer, 6th edition, vol. 1, 1987, pp. 9–10.

Römpp Chemie Lexikon, 9th edition, vol. 3, 1990, pp. 1894–1895, paragraph "Hydrotalcit".

*Primary Examiner*—Kimberly Jordan
*Attorney, Agent, or Firm*—Foley & Lardner

[57] ABSTRACT

An antacid composition comprises, as antacid ingredients, a hydrotalcite and dihydroxyaluminium aminoacetate in such a ratio that the former/the latter equals 30/70 to 90/10 (by weight). The composition may further comprises a readily acting or rapid effecting antacid ingredient such as a magnesium hydroxide in an amount of 10 to 50% by weight. The antacid composition is improved in antacid properties and rapid effecting properties, and is useful as a pharmaceutical composition comprising the antacid composition, a carrier, an additive, an additional pharmaceutically active ingredient and so on. The total amount of the antacid ingredients in the pharmaceutical composition may be 10% by weight or more. The pharmaceutical composition may be formed into a fine granule or a granule with utilizing granulation, or into a tablet by compression-molding.

21 Claims, 3 Drawing Sheets

ANTACID COMPOSITIONS

This application is a continuation, of application Ser. No. 08/288,608, filed Aug. 10, 1994, now abandoned.

FIELD OF THE INVENTION

The present invention relates to an antacid composition, particularly an antacid composition which shows no effect on a patient in hypoacidity or anacidity, and gives a fast or ready effect on a patient in hyperacidity or hyperchylia, and to a pharmaceutical composition comprising the antacid composition.

BACKGROUND OF THE INVENTION

Heart burn (pyrosis), sysphoria after meal, flatulent feeling have been considered to be mainly caused by hyperacidity or hyperchylia. Recently, however, it is reported that similar symptoms are appeared in case of hypoacidity or anacidity. Patients in hypoacidity or anacidity may frequently take a general gastrointestinal or gastroenteric drug or an antacid, on concluding only by subjective symptoms or signs. In such a case, however, the symptoms may rather take the turn for the worse. Therefore, it is preferable to show no effect on patients in hypoacidity and in anacidity, and to give effects only on patients in hyperacidity or hyperchylia. With regard to antacids suitable for such objects, for example, Japanese Patent Application Laid-Open No. 101520/1975 (JP-A-50-101520) discloses a method of coating an antacid ingredient with a coating composition which dissolves at pH 5-6 or less, and Japanese Patent Application Laid-open No. 210012/1984 (JP-A-59-210012) discloses an antacid coated with a coating composition which is soluble only in acidic region.

In these antacids, however, polymers used as the coating compositions, for instance, polyvinylacetal diethylaminoacetate [AEA (trade name), manufactured by Sankyo, Co., Ltd., Japan] and a dimethylaminoethylmethacrylate-methacrylate copolymer [Eudragit E (trade name), manufactured by Röhm Pharma GmbH, Germany] are expensive. Further, an organic solvent (for example, alcohols, acetone, methylene chloride and the like) employed for coating with the coating composition causes some problems such as safety and remaining of the organic solvent.

SUMMARY OF THE INVENTION

Accordingly, it is an object of the present invention to provide an antacid composition and a pharmaceutical composition which can dissolve in an acidic region to neutralize gastric acid and can suppress the pH increase in a neutral region, without a coating polymer and an organic solvent.

It is another object of the invention to provide an antacid composition and a pharmaceutical composition which can rapidly or readily adjust the pH to a neutral region by a simple composition.

A yet another object of the invention is to provide an antacid composition and a pharmaceutical composition by which the gastric acid can rapidly or readily be neutralized.

It is a further object of the present invention to provide an antacid composition and a pharmaceutical composition which can rapidly or readily neutralize in an acidic region and can maintain in a neutral region regardless of the acidity or the initial pH.

After much research to accomplish the above objects, the inventors of the present invention found that although a hydrotalcite and dihydroxyaluminium aminoacetate may not show antacid properties when used singly, they can exhibit or show higher antacid properties and rapid effecting properties when used in combination, and that the above-mentioned characteristics or properties can be further improved by adding a rapid effecting antacid ingredient such as a magnesium hydroxide. The present invention has been accomplished based on these findings.

Thus, the antacid composition and the pharmaceutical composition of the present invention comprise a hydrotalcite and dihydroxyaluminium aminoacetate as antacid ingredients.

DETAILED DESCRIPTION OF THE INVENTION

Figure 1:
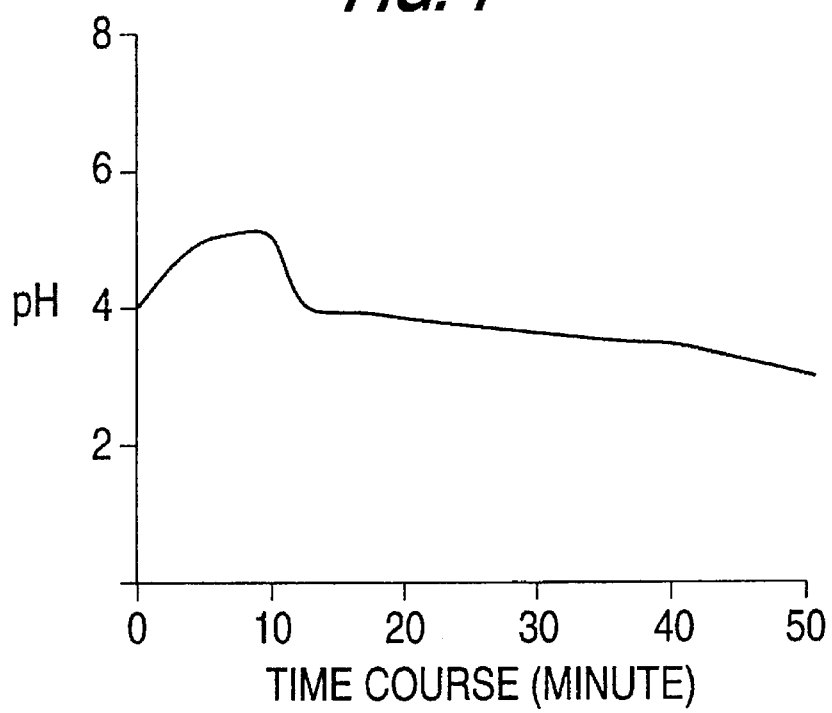
FIG. 1 is a graph illustrating the results in an acidic solution test in Example 1.

As used throughout this specification, the term "antacid composition" refers to a composition which is formed with only antacid ingredients. The term "pharmaceutical composition" means, including an antacid, a composition further comprising, in addition to the antacid composition, an active ingredient other than antacid ingredient and other ingredient such as an additive.

The hydrotalcite, as an antacid ingredient, belongs to a basic magnesium carbonate and is characterized by having a prolonged action with regard to antacid properties. The hydrotalcite may be a naturally-occurring hydrotalcite or a synthetic hydrotalcite. Preferred hydrotalcite includes the synthetic hydrotalcite. Such synthetic hydrotalcite can be commercially available, for instance, as Alcamac (trade name of Kyowa Chemical Co., Ltd., Japan).

Typical example of the hydrotalcite may be represented by the composition formula $Mg_6Al_2(OH)_{16}CO_3$, and at least a part of aluminium (Al) may be substituted with other metal such as iron (Fe). A mixture of a hydrotalcite containing Al and a hydrotalcite containing other metal such as Fe, in the composition formula, can also be used as the hydrotalcite.

Dihydroxyaluminium aminoacetate as an antacid has characteristics of elongated antacid actions. Dihydroxyaluminium aminoacetate may be commercially available as Glycinal (trade name of Kyowa Chemical Co., Ltd., Japan).

Though respective or separate use of the hydrotalcite and dihydroxyaluminium aminoacetate can not achieve the consistent or compatibility of the antacid properties and the prolonged action properties, a use of the both ingredients in combination can afford an antacid composition having higher antacid properties and readily or immediately acting properties.

The ratio of the hydrotalcite relative to dihydroxyaluminium aminoacetate can be selected from a suitable range as far as the antacid properties and the readily acting or rapid effecting properties are not adversely affected, and is for example, such that the former/the latter equals about 30/70 to 90/10 (by weight), preferably about 40/60 to 80/20 (by weight), and more preferably about 45/55 to 70/30 (by weight).

Preferred antacid composition may further comprise a rapid effecting antacid ingredient. As examples of the rapid effecting antacid ingredient, there may be mentioned a magnesium hydroxide, a magnesium oxide, magnesium carbonate, sodium carbonate, sodium hydrogen-carbonate and so on. These rapid effecting antacid ingredients can be used singly or in combination.

Typical example of the readily acting or rapid effecting antacid ingredient includes a magnesium hydroxide. Such magnesium hydroxide may be on the market as, for example, Kyowasuimagu (trade name of Kyowa Chemical Co., Ltd., Japan).

When the rapid effecting antacid ingredient is used in combination with the antacid ingredients as above, the antacid properties and the rapid effecting properties can further be enhanced, though a use of the rapid effecting antacid ingredient alone can not achieve the desired functions. The amount of the rapid effecting antacid ingredient may be selected from an adequate range as far as the rapid effecting properties may not be harmed, and is about 10 to 50% by weight, preferably about 15 to 45% by weight and more preferably about 20 to 40% by weight based on the total weight of the antacid ingredients.

The antacid composition of the present invention may, if necessary, further comprise other antacid ingredient. Examples of the other antacid ingredient include aluminum-containing antacids such as an aluminum hydroxide gel, an aluminum hydroxide, an aluminium silicate, a magnesium metasilicate aluminate, a magnesium silicate aluminate and an aluminium sulfate; calcium-containing antacids such as calcium hydroxide; magnesium-containing antacids such as a magnesium silicate; amino acetate and the like.

The antacid ingredient such as the hydrotalcite, dihydroxyaluminium aminoacetate and the rapid effecting antacid ingredient may usually be used in a particulate form such as a powdery or granular form, particularly in a powdery form.

The antacid composition of the present invention has actions of dissolving and neutralizing the gastric acid in the acidic region, and of suppressing or minimizing the pH increase in the neutral region, and has features that when taken by a patient in hypoacidity or anacidity, the antacid sparingly dissolves in the stomach, and on the contrary, when taken by a patient in hyperacidity or hyperchylia, the antacid readily dissolves and neutralizes an excess of the acid, and thus the antacid properties can effectively be shown.

As described above, the antacid composition of the present invention possesses higher antacid properties and readily acting or rapid effecting properties, and is useful for a pharmaceutical composition. The pharmaceutical composition may be an antacid containing, for instance, an additive in addition to the antacid composition, and may be a medicament or pharmaceutical preparation further comprising a pharmaceutically active ingredient other than antacid ingredient (hereinafter referred to as additional pharmaceutically active ingredient) such as a digestant, an analgesic and others.

As the additive, conventional additives can be used. Such additives include excipients such as lactose, corn starch, talc, crystalline cellulose [e.g. Avicel (trade name), etc.], powder sugar, magnesium stearate, mannitol, light silicic anhydride, calcium carbonate, L-cysteine and so on; binders such as starch, α-starch, sucrose, gelatin, gum arabic, methylcellulose, carboxymethylcellulose, carboxymethylcellulose sodium, hydroxypropylcellulose, hydroxypropylmethylcellulose, polyvinylpyrrolidone, pullulan, dextrin, etc.; disintegrators such as carboxymethylcellulose calcium [for example, ECG 505 (trade name), etc.], low-substituted hydroxypropylcellulose and croscarmellose sodium [for instance, Acdisol (trade name), and the like]; surfactants including an anionic surfactant, a nonionic surfactant [e.g. Pullronic F68 (trade name), etc.]; mucosaprotective agents such as sucralfate and the like; lipids (for instance, higher fatty acids such as stearic acid; higher alcohols such as stearyl alcohol; fats and oils such as glycerol fatty acid esters, a hardened cottonseed oil, a hardened caster oil, a hardened soybean oil; waxes such as carnauba wax, microcrystalline wax and so on); colorants; corrigents and flavors; adsorbents; preservatives; wetting agents; antistatic agents; disintegration retarders; and others.

The excipient and binder may practically be used as carriers for a preparation, and the disintegrator may also be employed in many cases. The proportion of the additive, particularly of the carrier is, for instance, about 10 to 70% by weight, preferably about 15 to 65% by weight and more preferably about 20 to 60% by weight based on the total weight of the composition.

In the pharmaceutical composition, the species of the additional pharmaceutically active ingredient is not specifically restricted and including not only drugs or pharmaceutical preparations for human being but also animal drugs. Examples of such additional pharmaceutically active ingredient include drugs for digestive system such as digestants, stomachics, anti-peptic ulcer agents and drugs for controlling intestinal function. The active ingredient may be a crude drug or Chinese medicine. The antacid composition may frequently be used in combination with, for example, a gastrointestinal drug such as a digestant, a stomachic and an anti-peptic ulcer agent. These drugs for digestive system can be used singly or in combination.

Examples of the digestant include a starch digestive enzyme (amylolytic enzyme) such as diastase, ptyalin and amylase, a protein digestive enzyme (for example, a proteolytic enzyme) such as pepsin, trypsin and papain, a lipid digestive enzyme (e.g. a lipase), pancreatin, hydrochloric acid lemonade, ursodesoxycholic acid, bile powder and the like.

The stomachic includes, for instance, betaine hydrochloride, glutamic acid hydrochloride, l-menthol, carnitine chloride, dried yeast and so on.

As examples of the anti-peptic ulcer agent, there may be mentioned azulene sodium sulfonate, aldioxa, L-glutamine, potassium copper chlorophyllin, methyl methionine sulfonium chloride, dimethylpolysiloxane and others. The intestinal function controlling agent includes, for example, a live cell (e.g. bacteria, yeast, etc.) ingredient for intestinal function controlling.

Examples of the crude drug or Chinese medicine include scopolia extract, cinnamon bark (cinnamomi cortex), magnolia bark (magnoliae cortex), ginger (zingiberis rhizoma), atractylodes lancea rhizome (atractylodis lanceae rhizoma), rhubarb (rhei rhizoma), clove (caryophylli flos), citrus unshiu peel (aurantii nobilis pericarpium), ginseng (ginseng radix), *Mallotus japonicus*, phellodendron bark (phellodendri cortex), swertia herb (swertia japonica), corydalis tuber (corydalis tuber), licorice root (glycyrrhizae radix), peony root *(Paeonia lactiflora,* paeoniae radix), gentian (Gentianae radix), Japanese gentian (gentianae scabrae radix), coptis rhizome (coptidis rhizoma), dried bitter orange peel (aurantii pericarpium), fennel (foeniculi fructus), zanthoxylum fruit (zanthoxyli fructus) and so on.

The content of the additional pharmaceutically active ingredient may be selected from a suitable range depending on the species of the active ingredient, and is, for instance, about 0.001 to 50% by weight, preferably about 0.01 to 40% by weight and more preferably about 0.1 to 35% by weight based on the total weight of the pharmaceutical composition.

The content of each of the antacid ingredient and the total amount of the antacid composition in the pharmaceutical composition can be selected from a wide range so far as being an effective amount. The total amount of the antacid composition formed with the hydrotalcite and dihydroxyaluminium aminoacetate is, for example, about 5 to 80% by weight, preferably about 10 to 60% by weight, and more preferably about 20 to 50% by weight based on the total weight of the pharmaceutical composition. The amount of the rapid effecting antacid ingredient is, for instance, about 2 to 30% by weight, and preferably about 5 to 25% by weight based on the total weight of the pharmaceutical composition. The proportion of magnesium hydroxide, as a preferable rapid effecting antacid ingredient, is, for example, about 5 to 30% by weight, and preferably about 7 to 25% by weight based on the total weight of the pharmaceutical composition.

Based on the total weight of the pharmaceutical composition, the total amount of the antacid composition composed of the hydrotalcite, dihydroxyaluminium aminoacetate and the rapid effecting antacid ingredient is, for example, about 10% by weight or more, preferably about 20 to 70% by weight, and more preferably about 25 to 60% by weight.

The form of the pharmaceutical composition is not critical, and may be a powdery mixture containing the antacid composition and an additive, and if required, an additional pharmaceutically active ingredient. Preferred pharmaceutical composition may be compounded to form a pharmaceutical preparation. Examples of the pharmaceutical preparation include a solid pharmaceutical preparation such as a granulated preparation (for instance, a fine granule, a granule, a powder, a pill and the like), a tablet obtainable by compression-molding a composition containing, for example, the powdery mixture or the granulated preparation, a capsule obtainable by filling a capsule, for instance, with the granulated preparation and so on. The pharmaceutical preparation may frequently be a fine granule, a granule, a tablet or the like.

The average particle or grain size (diameter) of the fine granule is, for example, about 10 to 500 μm and preferably about 100 to 500 μm, and the average particle or grain size (diameter) of the granule is, for instance, about 300 to 1,500 μm and preferably about 500 to 1,500 μm.

The pharmaceutical preparation containing the antacid composition can be prepared by a conventional manner depending on the form of the preparation. By way of illustrating, the pharmaceutical preparation may be produced by, for instance, a commonly used manner such as extruding granulation, fluidizing granulation, spray granulation and tumbling granulation, with the use of, for example, the antacid composition, an additive, and if desired an additional pharmaceutically active ingredient. Granulation can be carried out by either of a dry granulation or a wet granulation. In the wet granulation, a solvent having a higher safety (for instance, an alcohol such as ethanol, water or the like) or a solution of the binder in the solvent as above may be employed in many cases.

The following examples are merely intended to illustrate the present invention in further detail and should not be construed as defining the scope of the invention.

EXAMPLES

Example 1

A mixture of 550 g of a synthetic hydrotalcite, 550 g of dihydroxyaluminium aminoacetate, 550 g of a magnesium hydroxide, 1,000 g of lactose, 585 g of corn starch, 40 g of crystalline cellulose and 20 g of carboxymethylcellulose calcium (ECG 505) was wet-kneaded by a conventional method using 900 ml of an aqueous Solution containing 5 g of Pullronic F68.

The kneaded was passed through a screen of 0.8 mmϕ of an extrusion granulator (manufactured by Kikusui Seisakusho Co., Ltd., Japan; RG-C125). The resultant product was rounded with the use of a Marumerizer (manufactured by Fuji Paudal Co., Ltd., Japan; QJ-230) and dried to give spherical granules.

The antacid activity of the obtained granules was determined by the following modified Fuchs test which is usually employed for an antacid activity test as a test procedure for granules.

(1) An acidic solution test

To 50 ml of 0.1N hydrochloric acid was added 1 g of a sample at 37° C. with stirring. After 10 minutes from addition of the sample, 0.1N hydrochloric acid was poured into the mixture in a ratio of 2 ml per minute. The temperature of the mixture was maintained at 37° C. throughout the test, and the pH was determined continuously.

(2) Purified water test

One gram of the sample was added to 50 ml of purified water with stirring at 37° C., and the pH was measured continuously.

Figure 2:
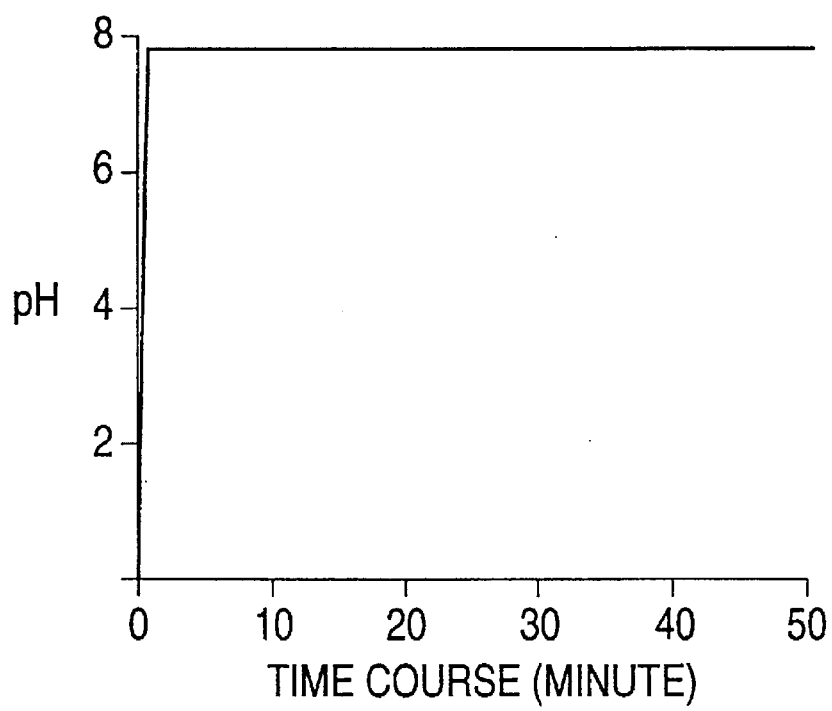
FIG. 2 is a graph illustrating the results in a purified water test in Example 1.

The results are shown in FIG. 1 and FIG. 2. As apparent from FIGS. 1 and 2, in the acidic solution test, the neutralization was reached within about 10 minutes, and the duration of being remained in the region of pH 3–6 was about 52 minutes, and in the purified water test, the pH was maintained at 7.8. Therefore, the granules can readily or immediately neutralize in an acidic region, and can suppress or inhibit the increase of the pH in a neutral region.

Example 2

Figure 3:
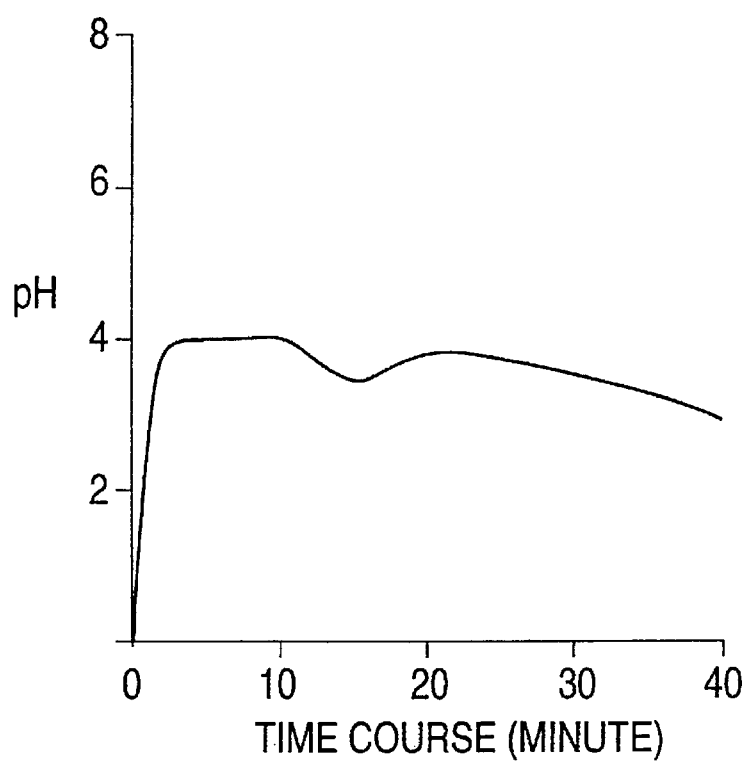
FIG. 3 is a graph showing the results in the acidic solution test in Example 2.
Figure 4:
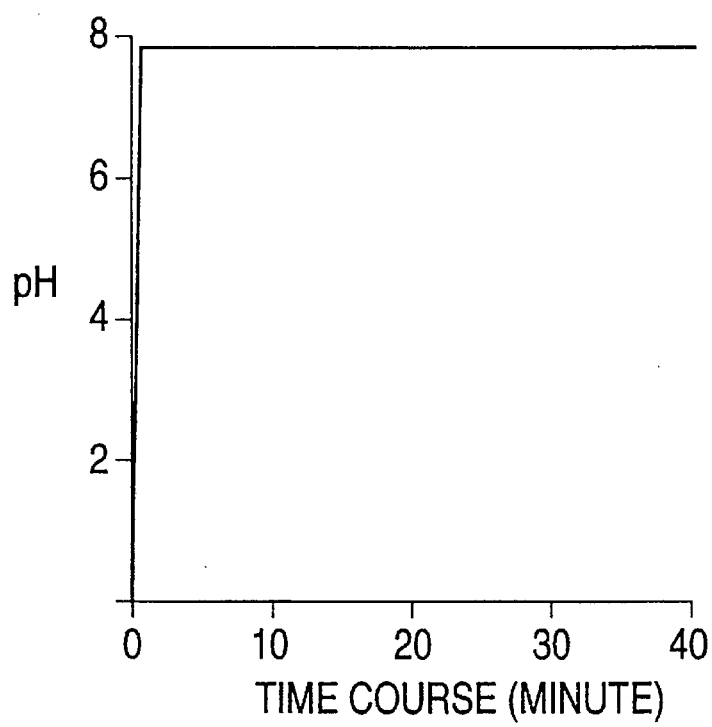
FIG. 4 is a graph showing the results in the pure-water test in Example 2.

The antacid activity of a mixed powder of a synthetic hydrotalcite (250 mg) and dihydroxyaluminium aminoacetate (250 mg) was determined in the same manner as in Example 1, and the results are set forth in Table 1, FIG. 3 and FIG. 4.

The amount of each of the antacid ingredients was corresponding to the amount of acid consume capacity or titer of 120 ml which is capable of neutralizing 120 ml of the acid. The result in the acidic solution test is the value measured or determined after 10 minutes from the initial of the test, and the result in the purified water test is the value measured after 30 minutes from the initial of the test.

As clearly shown in FIG. 3 and FIG. 4, in the acidic solution test, the neutralization can be reached within about 10 minutes, and the duration being remained in the region of pH 3–6 was about 40 minutes, and in the purified water test, the pH was remained at 7.8. Therefore, the sample can readily or immediately neutralize in the acidic region, and can suppress or inhibit the increase of the pH in the neutral region.

Comparative Examples 1 to 3

The procedure of Example 1 was followed to determine the antacid activity, except for a single use of a synthetic hydrotalcite (Comparative Example 1), dihydroxyaluminium aminoacetate (Comparative Example 2) or magnesium hydroxide (Comparative Example 3) respectively. The results are set forth in Table 1 with the results in Examples 1 and 2.

The used amount of each of the antacid ingredients in the Comparative Examples corresponded to the amount of acid consume capacity or titer of 140 ml. The results in the Table 1 are the values measured after 10 minutes from the initial of the test for the acidic solution test and the values determined after 30 minutes from the initial of the test for the purified water test.

TABLE 1

|  | 0.1 N Hydrochloric acid (10 minutes-value) | Purified water (30 minutes-value) |
| --- | --- | --- |
| Example 1 | pH = 5.2 | pH = 7.8 |
| Example 2 | pH = 4.0 | pH = 7.8 |
| Comp. Ex. 1 | pH = 4.2 | pH = 8.2 |
| Comp. Ex. 2 | pH = 4.0 | pH = 7.2 |
| Comp. Ex. 3 | pH = 8.9 | pH = 10.1 |

As apparently shown in Table 1, when the synthetic hydrotalcite (Comparative Example 1) or magnesium hydroxide (Comparative Example 3) was used separately, the pH in the purified water test was increased remarkably, and it was difficult to maintain the pH within the neutral region. Dihydroxyaluminium aminoacetate (Comparative Example 2) affords comparatively good results with regard to the pH stability, but it lacks readily acting or rapid effecting properties.

Example 3

A vertical granulator (manufactured by Powrex Corporation, Japan; VG-10) was charged with 660 g of a synthetic hydrotalcite, 495 g of dihydroxyaluminium aminoacetate, 495 g of a magnesium hydroxide, 700 g of lactose, 170 g of low-substituted hydroxypropylcellulose, 300 g of corn starch and 90 g of Acdisol (croscarmellose sodium). The charged was wet-granulated by using a solution of 90 g of hydroxypropylcellulose in 700 ml of water, comminuted with a Power Mill (manufactured by Showa Kagakukikai Co., Ltd., Japan; P-3), and dried to give granules.

The resultant granules, 150 g of carboxymethylcellulose calcium (ECG 505) and 9 g of magnesium stearate were mixed by using a Tumble Mixer (product of Showa Kagakukikai Co., Ltd., Japan; TM-15) for 5 minutes. The resultant mixture was compression-molded or tabletted with the use of a rotary tablet machine (manufactured by Kikusui Seisakusho, Co., Ltd., Japan; 19K) to give tablets (diameter: 10 mm$\phi$; weight: 500 mg per tablet).

The determination procedure for the antacid activity of Example 1 was followed using the amount of the tablet corresponding to acid consume capacity of 140 ml. The pH after 10 minutes from the initial of the test in the acidic solution test (1) was 6.0, and the pH after 30 minutes from the beginning of the purified water test (2) was 7.9, thus the pH was maintained in the neutral region regardless of the initial pH.

Example 4

A vertical granulator was charged with 732 g of a synthetic hydrotalcite, 294 g of dihydroxyaluminium aminoacetate, 441 g of a magnesium hydroxide, 150 g of dried extract of citrus unshiu peel (aurantii nobilis pericarpium), 20 g of powdered extract of atractylodes lancea rhizome (atractylodis lanceae rhizoma), 17 g of powdered extract of magnolia bark (magnoliae cortex), 100 g of powdered extract of ginger (zinglberis rhizoma), 30 g of powdered extract of cloves (caryophylli flos), 300 g of dl-carnitine chloride, 150 g of powdered extract of licorice root (glycyrrhizae radix), 1,600 g of D-sorbitol, 80 g of light silicic anhydride (Syloid 266), 50 g of lactose and 40 g of hydroxypropylcellulose. The charged was granulated with adding an alcohol solution containing 16 g of l-menthol, and dried with the use of a vacuum drier (manufactured by Kusunoki Seisakusho, Japan). The dried granulated products were comminuted by using a Power Mill (manufactured by Showa Kagakukikai Co., Ltd., Japan; P-3) to give fine granules. The fine granules contain, per 3 packages, 732 mg of the synthetic hydrotalcite, 294 mg of dihydroxyaluminium aminoacetate and 441 mg of magnesium hydroxide, corresponding to the acid consume capacity of 420 ml.

Figure 5:
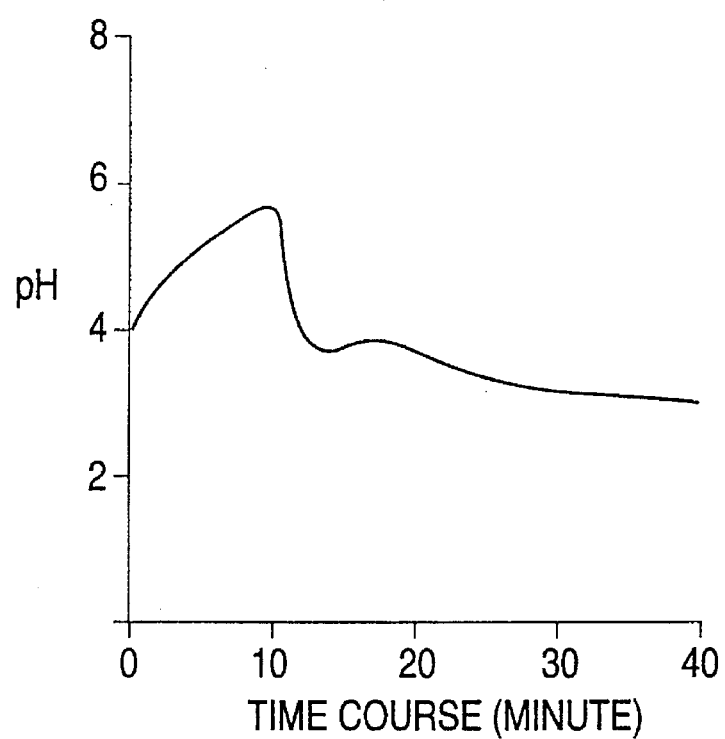
FIG. 5 is a graph illustrating the results in the acidic solution test in Example 4.
Figure 6:
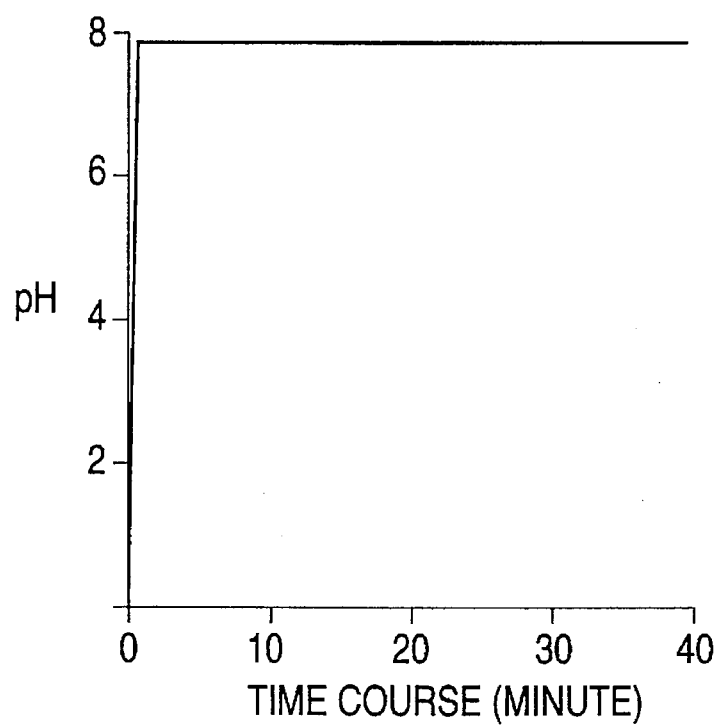
FIG. 6 is a graph showing the results in the purified water test in Example 4.

The antacid activity of the fine granules was determined in the same manner as in Example 1, and the results are set forth in FIG. 5 and FIG. 6. As apparent from FIGS. 5 and 6, in the acidic solution test, the neutralization was reached within about 10 minutes, and the duration retained or maintained in the region of pH 3–6 was about 40 minutes and in the purified water test, the pH was maintained at 7.9. Therefore, the sample can readily or immediately neutralize in the acidic region, and can suppress or restrain the increase of the pH in the neutral region.

Example 5

A kneader (manufactured by Hata Works Co., Ltd., Japan) was charged with 450 g of powdery synthetic aluminium silicate and 25 g of powdery light silicic anhydride. To the charged was added and adsorbed a solution of 450 g of dl-carnitine chloride in 700 ml of water. The resultant wet powder was dried using a vacuum drier (manufactured by Kusunoki Seisakusho Co., Ltd., Japan) and pulverized with an Atomizer (Fuji Paudal Co., Ltd., Japan; KII-2) to give an adsorbed powder.

A vertical granutator (manufactured by Powrex Corporation, Japan; FM-G25) was charged with 925 g of the adsorbed powder, 700 g of a synthetic hydrotalcite (VF), 450 g of a magnesium hydroxide, 300 g of dihydroxyaluminium aminoacetate (aluminum glycinate), 150 g of powdered extract of licorice root (glycyrrhizae radix), 150 g of dried extract of citrus unshiu peel (aurantii nobilis pericarpium), 200 g of powdered extract of atractylodes lancea rhizome (atractylodis lanceae rhizoma), 20 g of dried extract of magnolia bark (magnoliae cortex), 100 g of powdered extract of ginger (zingiberis rhizoma), 30 g of powdered extract of cloves (caryophylli flos), 1,000 g of D-sorbitol, 74 g of mannitol and 80 g of hydroxypropylcellulose (HPC). After mixing, the charged was granulated with addition of an alcoholic solution of 16 g of l-menthol. The granulated product was dried using a fluidized-bed drier (Powrex Corporation, Japan; FD5S) and sieved. To the sieved was added 5 g of light silicic anhydride as a fluidizing agent to give 4,200 g of the granules.

Example 6

A kneader (manufactured by Hata Works Co., Ltd., Japan) was charged with 350 g of a powdery synthetic aluminium silicate and 30 g of a powdery light silicic anhydride. An aqueous solution of 450 g of d-carnitine chloride in 240 ml of water was added and adsorbed to the charged under kneading. The mixture was dried with a vacuum drier (Kusunoki Seisakusho Co., Ltd., Japan) and pulverized by using an Atomizer (manufactured by Fuji Paudal Co., Ltd., Japan; KII-2) to give an adsorbed powder.

A mixture of 830 g of the adsorbed powder, 49.5 g of light silicic anhydride, 700 g of synthetic hydrotalcite (VF), 450 g of a magnesium hydroxide, 300 g of dihydroxyaluminium aminoacetate (aluminium glycinate), 125 g of powdered extract of licorice root (glycyrrhizae radix), 150 g of dried extract of citrus unshiu peel (aurantii nobilis pericarpium), 60 g of a powdery extract of atractylodes lancea rhizome (atractylodis lanceae rhizoma), 20 g of dried extract of magnolia bark (magnoliae cortex), 10 g of powdered extract of ginger (zingiberis rhizoma), 30 g of powdered extract of cloves (caryophylli flos), 99.5 g of croscarmellose sodium (Acdisol), 74 g of mannitol and 120 g of HPC-L (hydroxypropylcellulose-L) was granulated with the use of a high-shear mixer (Fukae Kogyo Co., Ltd., Japan). The granulated product was dried with a flow coater (manufactured by Freund Industries Co., Ltd.) and comminuted with a Power Mill (Showa Kagakukikai Co., Ltd., Japan; P-3S) to give a comminuted or classified powder. The comminuted or classified powder was flavored by adding a solution of 13 g of l-menthol in ethanol. The resultant powder (3,031 g) was mixed with 19 g of magnesium stearate as a lubricant and 100 g of croscarmellose sodium (Acdisol) using a Tumble Mixer (Showa Kagakukikai Co., Ltd., Japan; TM-15). The mixture was compression-molded with a rotary tablet machine (manufactured by Kikusui Seisakusho, Co., Ltd., Japan; correct 19K) provided with a punch having a curved surface of 9.5 mm$\phi$ to give tablets.

What is claimed is:

1. An antacid composition which comprises a hydrotalcite, dihydroxyaluminium aminoacetate and a magnesium hydroxide, wherein the amount of the magnesium hydroxide present in said antacid composition is 20 to 40% by weight based on the total weight of the hydrotalcite, dihydroxyaluminum aminoacetate and magnesium hydroxide.

2. An antacid composition according to claim 1, wherein the ratio of the hydrotalcite to dihydroxyaluminium aminoacetate is 30/70 to 90/10 (by weight).

3. An antacid composition according to claim 1, wherein the ratio of the hydrotalcite to dihydroxyaluminium aminoacetate is 40/60 to 80/20 (by weight).

4. An antacid composition according to claim 1, wherein the hydrotalcite is a basic magnesium carbonate represented by the composition formula $Mg_6Al_2(OH)_{16}CO_3$.

5. An antacid composition which comprises 60 to 80% by weight of the total weight of said antacid composition of a hydrotalcite and dihydroxyaluminium aminoacetate, and 20 to 40% by weight of a magnesium hydroxide, based on the total weight of the antacid composition, wherein the weight ratio of the hydrotalcite to dihydroxyaluminium aminoacetate is from 40/60 to 80/20.

6. An antacid composition according to claim 5, wherein the weight ratio of the hydrotalcite to dihydroxyaluminium aminoacetate is from 45/55 to 70/30.

7. A pharmaceutical composition which comprises an antacid composition comprising a hydrotalcite, dihydroxyaluminium aminoacetate and a magnesium hydroxide, wherein the amount of the magnesium hydroxide present in said antacid composition is 20 to 40% by weight based on the total weight of the hydrotalcite, dihydroxyaluminium aminoacetate and magnesium hydroxide.

8. A pharmaceutical composition according to claim 7, wherein the total weight of the hydrotalcite and dihydroxyaluminium aminoacetate is 5 to 80% by weight based on the total weight of the pharmaceutical composition.

9. A pharmaceutical composition according to claim 7, wherein the total amount of the hydrotalcite, dihydroxyaluminium aminoacetate and the magnesium hydroxide is 10% by weight or more, based on the total weight of the pharmaceutical composition.

10. A pharmaceutical composition according to claim 9, wherein the content of the magnesium hydroxide is 2 to 30% by weight, based on the total weight of the pharmaceutical composition.

11. A pharmaceutical composition according to claim 9, wherein the content of the magnesium hydroxide is 5 to 30% by weight, based on the total weight of the pharmaceutical composition.

12. A pharmaceutical composition according to claim 9, which comprises the hydrotalcite, dihydroxyaluminium aminoacetate, the magnesium hydroxide, and an additive.

13. An pharmaceutical composition according to claim 12, which comprises 10 to 60% by weight of the total weight of the hydrotalcite and dihydroxyaluminium aminoacetate, and 5 to 25% by weight of the magnesium hydroxide and 15 to 65% by weight of the additive, based on the total weight of the pharmaceutical composition, wherein the ratio of the hydrotalcite to dihydroxyaluminium aminoacetate is from 40/60 to 80/20 (by weight).

14. A pharmaceutical composition according to claim 13, wherein the weight ratio of the hydrotalcite to dihydroxyaluminium aminoacetate is from 45/55 to 70/30.

15. A pharmaceutical composition according to claim 12, wherein the total amount of the hydrotalcite, dihydroxyaluminium aminoacetate and the magnesium hydroxide is 20 to 70% by weight, based on the total weight of the pharmaceutical composition.

16. A pharmaceutical composition according to claim 12, wherein the content of the magnesium hydroxide is 7 to 25% by weight, based on the total weight of the pharmaceutical composition.

17. A pharmaceutical composition according to claim 12, which further comprises an additional pharmaceutically active ingredient.

18. A pharmaceutical composition according to claim 17, wherein the additional pharmaceutically active ingredient is a drug for digestive system.

19. A pharmaceutical composition according to claim 17, wherein the additional pharmaceutically active ingredient is at least one member selected from the group consisting of a digestant, a stomachic, an anti-peptic ulcer agent, a drug for controlling intestinal function.

20. A pharmaceutical composition according to claim 17, which comprises 0.001 to 50% by weight of the additional pharmaceutically active ingredient and 20 to 60% by weight of at least one additive selected from an excipient, a binder and a disintegrator.

21. A pharmaceutical composition according to claim 7, which is a fine granule, a granule or a tablet.

* * * * *